United States Patent
Tsumori et al.

(10) Patent No.: US 10,357,415 B2
(45) Date of Patent: Jul. 23, 2019

(54) SURGICAL OPERATION TABLE

(71) Applicant: MIZUHO Corporation, Tokyo (JP)

(72) Inventors: Osamu Tsumori, Sakura (JP); Kei Aoki, Sakura (JP)

(73) Assignee: MIZUHO Corporation, Tokyo (JP)

(*) Notice: Subject to any disclaimer, the term of this patent is extended or adjusted under 35 U.S.C. 154(b) by 21 days.

(21) Appl. No.: 15/508,986

(22) PCT Filed: Sep. 2, 2015

(86) PCT No.: PCT/JP2015/074922
§ 371 (c)(1),
(2) Date: Mar. 6, 2017

(87) PCT Pub. No.: WO2016/039233
PCT Pub. Date: Mar. 17, 2016

(65) Prior Publication Data
US 2017/0252247 A1    Sep. 7, 2017

(30) Foreign Application Priority Data

Sep. 8, 2014 (JP) ................................ 2014-182725

(51) Int. Cl.
| | |
|---|---|
| A61G 13/00 | (2006.01) |
| A61G 13/06 | (2006.01) |
| A47B 13/00 | (2006.01) |
| A61G 13/04 | (2006.01) |
| A61B 6/04 | (2006.01) |
| A61G 13/08 | (2006.01) |
| A61G 7/008 | (2006.01) |

(52) U.S. Cl.
CPC ............ *A61G 13/04* (2013.01); *A61G 13/06* (2013.01); *A61G 13/08* (2013.01); *A47B 13/00* (2013.01); *A61B 6/04* (2013.01); *A61G 7/008* (2013.01)

(58) Field of Classification Search
CPC ........ A61G 13/02; A61G 13/04; A61G 13/06; A61G 13/08; A61G 7/008; A61B 6/04; A61B 6/0407; A47B 13/00
See application file for complete search history.

(56) References Cited

U.S. PATENT DOCUMENTS 3,206,188 A * 9/1965 Douglass, Jr. ......... A61G 13/02
5/607
3,302,022 A * 1/1967 Brenner ............... A61B 6/0457
108/5

(Continued)

FOREIGN PATENT DOCUMENTS

JP    2001-120609 A    5/2001
JP    2004-073616 A    3/2004

*Primary Examiner* — Nicholas F Polito
*Assistant Examiner* — Rahib T Zaman
(74) *Attorney, Agent, or Firm* — Sughrue Mion, PLLC

(57) ABSTRACT

A surgical operation table is provided, which is capable of crosswise turning a table without changing a position of a patient as much as possible. In a surgical operation table S including a table 15 for laying a patient thereon, motion mechanism sections 35, 20, 25, 70, 60, 65 and 80 that slide, crosswise turn, lengthwise turn, and elevate the table 15, and a base 2 that supports the table 15 via the motion mechanism sections 35, 20, 25, 70, 60, 65 and 80, position holding device is included, which crosswise turns or lengthwise turns the table 15 without changing the position of a head part of the patient laid on the table 15.

5 Claims, 13 Drawing Sheets

(56) References Cited

U.S. PATENT DOCUMENTS

| | | | | |
|---|---|---|---|---|
| 3,806,109 | A * | 4/1974 | Weber | A61G 13/02 |
| | | | | 378/209 |
| 3,868,103 | A * | 2/1975 | Pageot | A61G 13/02 |
| | | | | 137/596 |
| 4,195,829 | A * | 4/1980 | Reser | A61G 13/02 |
| | | | | 5/607 |
| 4,474,364 | A * | 10/1984 | Brendgord | A61G 13/08 |
| | | | | 5/613 |
| 4,865,303 | A * | 9/1989 | Hall | A61G 13/02 |
| | | | | 5/614 |
| 5,778,467 | A * | 7/1998 | Scott | A61G 13/009 |
| | | | | 5/612 |
| 6,502,261 | B1 * | 1/2003 | Harwood | A61B 6/0457 |
| | | | | 108/145 |
| 6,681,423 | B2 * | 1/2004 | Zachrisson | A61G 13/04 |
| | | | | 5/601 |
| 7,000,271 | B2 * | 2/2006 | Varadharajulu | A61B 6/0457 |
| | | | | 378/209 |
| 8,424,133 | B1 * | 4/2013 | Rossi | A61B 6/0442 |
| | | | | 5/601 |
| 2008/0134434 | A1 | 6/2008 | Celauro | |
| 2013/0111666 | A1 | 5/2013 | Jackson | |
| 2014/0068861 | A1 * | 3/2014 | Jackson | A61G 13/04 |
| | | | | 5/601 |

* cited by examiner

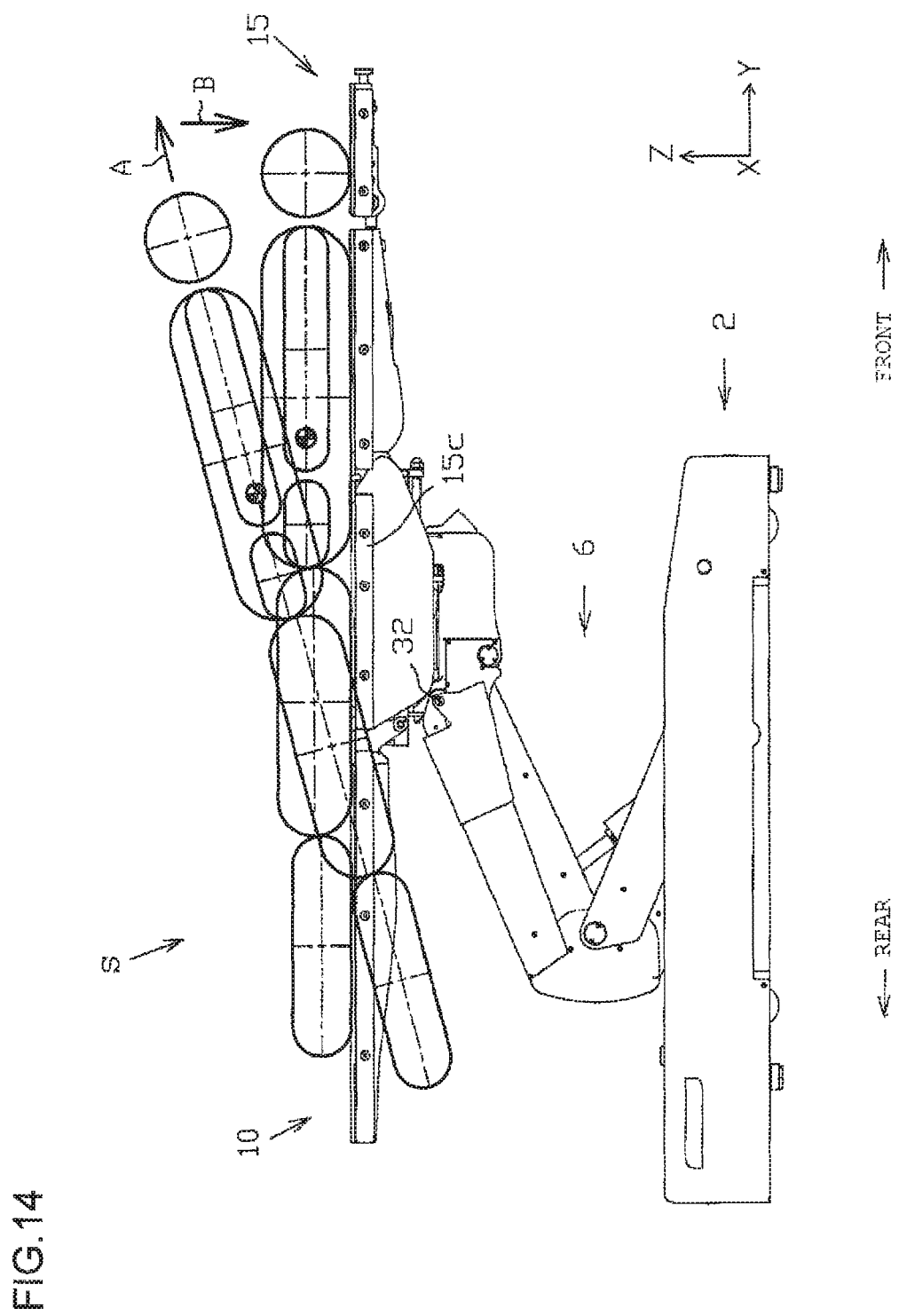

SURGICAL OPERATION TABLE

CROSS REFERENCE TO RELATED APPLICATIONS

This application is a National Stage of International Application No. PCT/JP2015/074922 filed Sep. 2, 2015, claiming priority based on Japanese Patent Application No. 2014-182725 filed Sep. 8, 2014, the contents of all of which are incorporated herein by reference in their entirety.

TECHNICAL FIELD

The present invention relates to a surgical operation table, and particularly relates to a surgical operation table in which a table where a patient is laid is inclinable.

BACKGROUND ART

A surgical operation table is required to be provided with a function of being able to freely change a height and an inclination of a table on which a patient is laid, because the surgical operation table needs to move a specific part of the patient to a position where a doctor can easily perform treatment on the specific part of the patient, and there has been conventionally known a surgical operation table provided with an elevating function and an inclining function for a table (refer to Patent Literature 1).

CITATION LIST

Patent Literature

Patent Literature 2: Japanese Patent Laid-Open No. 2004-73616

SUMMARY OF INVENTION

Technical Problem

Incidentally, when a surgical operation for a head is performed by using an endoscope, a microscope and the like with a surgical operation table of this kind, it is convenient because the table can be inclined at a predetermined angle and fixed, but when a necessity for crosswise turning or lengthwise turning of a posture of a patient arises during the surgical operation or after the head part of the patient is fixed, there arises the problem of being unable to turn the table easily because the position of the head part moves if the table is turned.

Thus, in order to solve an example of the problem like this, the present application has an object to provide a surgical operation table capable of crosswise turning or lengthwise turning a table without changing a position of a patient as much as possible.

Solution to Problem

In order to solve the above described problem, a surgical operation table (S) according to claim 1 is a surgical operation table including a table (15) for laying a patient thereon, motion mechanism sections (35, 20, 25, 70, 60, 65, 80) that slide, crosswise turn, lengthwise turn and elevate the table, and a base (2) that supports the table via the motion mechanism sections, and includes a position holding device that crosswise turns or lengthwise turns the table without moving a position of a head part of the patient that is laid on the table.

Further, the surgical operation table according to claim 2 is the surgical operation table according to claim 1, wherein the position holding device slides the table in an opposite direction from a crosswise turning direction of the table at a time of a crosswise turning motion of the table.

Further, the surgical operation table according to claim 3 is the surgical operation table according to claim 1 or claim 2, wherein the position holding device, in a case of lengthwise turning the table from a horizontal state, slides the table in a forward direction and elevates the table at a time of a lengthwise turning motion of the table, and in a case of returning the table to the horizontal state from a lengthwise turned state, slides the table in a rearward direction and elevates the table at a time of the lengthwise turning motion of the table.

Further, the surgical operation table according to claim 4 is the surgical operation table according to claim 2 or 3, wherein at least a slide motion of the table is performed simultaneously with a crosswise turning or a lengthwise turning motion of the table.

Further, the surgical operation table according to claim 5 is the surgical operation table according to any one of claims 1 to 4, and includes a cylinder device that crosswise turning or lengthwise turning the table by supplying or discharging a working oil and extending and contracting a rod by a pressure of the working oil, and another cylinder device that is supplied with a working oil that is discharged by an extending and contracting motion of the rod by the first cylinder device, and slides the table by extending and contracting a rod by a pressure of the working oil.

Advantageous Effects of Invention

Since the position of a patient does not change even when the table is inclined, burdens on the patient and a doctor can be reduced especially at the time of adopting a surgical operation of a head by using an endoscope, a microscope and the like.

BRIEF DESCRIPTION OF DRAWINGS

FIG. 10 is a schematic view for explaining a motion in a longitudinal direction of the table.

FIG. 14 is a schematic view for explaining an isocenter function at the time of the lengthwise turning motion.

DESCRIPTION OF EMBODIMENTS

Hereinafter, a mode for carrying out the present invention will be described based on an embodiment of the present invention illustrated in the accompanying drawings. Note that in the following explanation of a surgical operation table S, a left-right direction illustrated in FIG. 1 will be described as a Y-direction of the surgical operation table, a top-bottom direction will be described as a Z-direction of the surgical operation table, and a front-depth direction will be described as an X-direction of the surgical operation table. Further, the Y-direction will be described as a longitudinal direction of the surgical table, and the X-direction will be described as a crosswise direction of the surgical table.

Further, in the following explanation, a working oil refers to a fluid that is used as a power transmission medium in a hydraulic cylinder device.

Although the surgical operation table S of the present embodiment is favorably used at a time of adopting a surgical operation of a head by using an endoscope, a microscope and the like, the surgical operation table S is not limited to this field, and it is also possible to use the surgical operation table as an ordinary surgical operation table, and an ordinary treatment table.

Figure 1A:
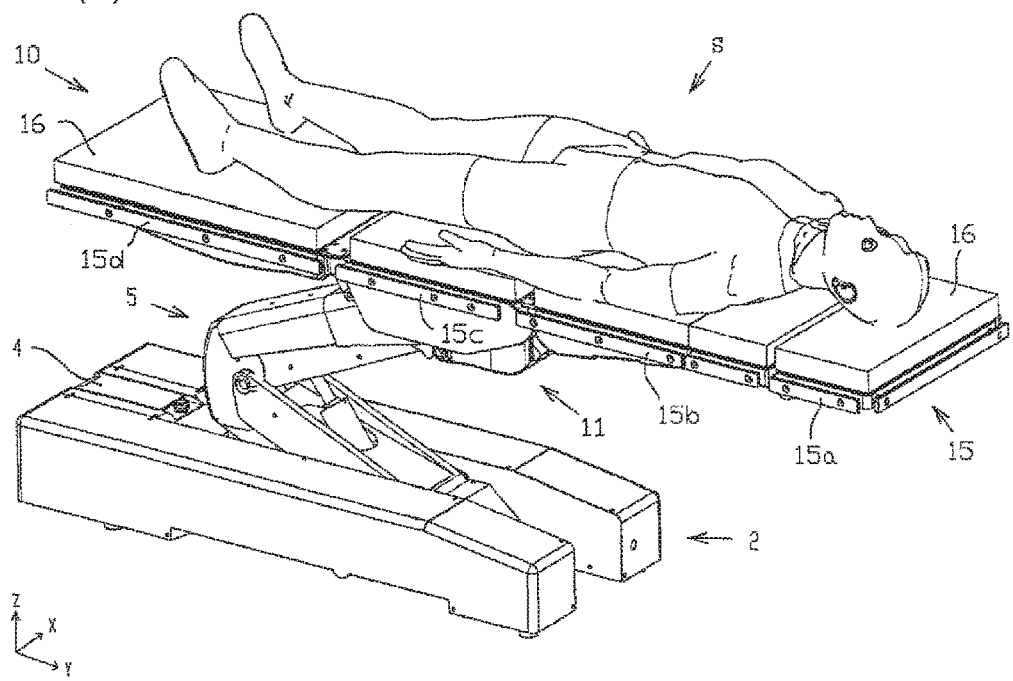
FIG. 1 illustrates an outside view example of a surgical operation table, FIG. 1(*a*) is a perspective view of the surgical operation table in a state where a table is made horizontal, and FIG. 1(*b*) is a perspective view of the surgical operation table in a state where the table is bent.
Figure 1B:
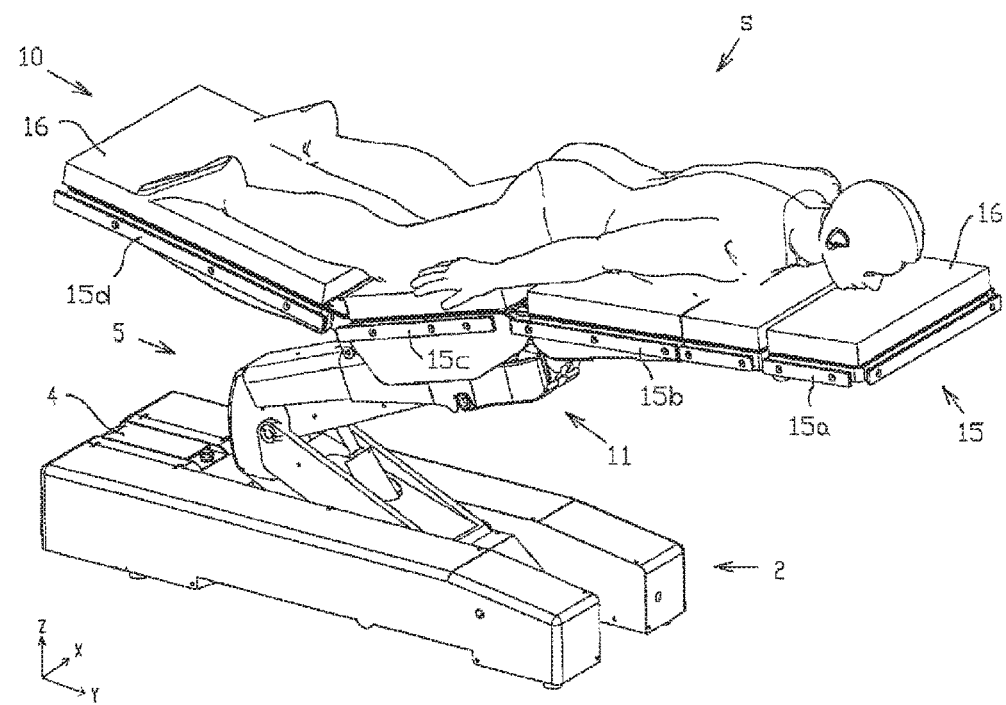
Figure 2A:
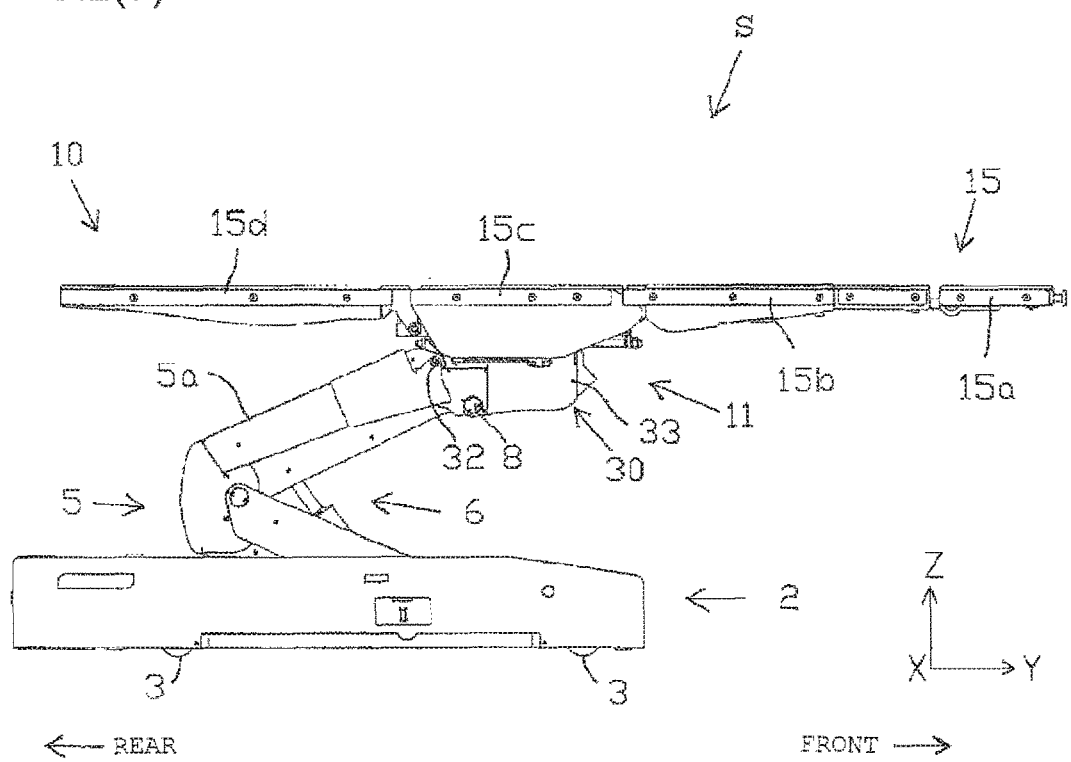
FIG. 2 is a schematic view illustrating an elevating motion of the surgical operation table, FIG. 2(*a*) is a side view at a time of the table being adjusted to be high, and FIG. 2(*b*) is a side view at a time of the table being made the lowest.
Figure 2B:
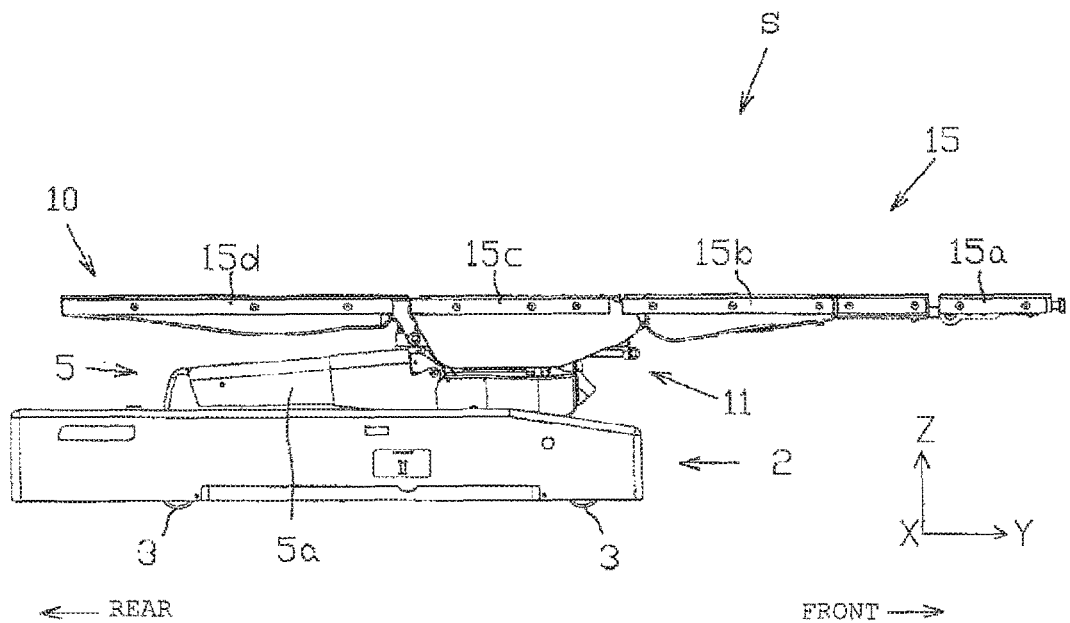

As illustrated in FIG. 1 and FIG. 2, the surgical operation table S includes a base 2 that is placed on a floor of a surgical operation room, a column 5 that is raised from the base 2, and a table unit 10 that is mounted on the column 5.

Further, as illustrated in FIG. 2, casters 3 are attached to a lower part of the base 2, and the casters 3 enable the surgical operation table S to move freely on a floor surface of the surgical operation room.

Note that the casters 3 are not indispensable components, and are provided in accordance with necessity. As for movement of the surgical operation table S which is provided with no caster 3, the surgical operation table S is placed on a predetermined stand or the like provided with rollers that are generally used at a time of carrying things, and is carried to a predetermined surgical operation room, and thereafter, the surgical operation table S is taken down from the stand and is installed.

Note that a control device or the like for electrically controlling a motion of the surgical operation table S is housed inside the base 2, and a touch panel type display element 4 for operating the surgical operation table S is provided on a rear upper surface. Further, the surgical operation table S is additionally provided with a remote controller which is electrically connected to the control device and has buttons for electrically controlling the surgical operation table S disposed thereon. It is possible for a user to cause the surgical operation table S to perform motions by using the remote controller or the display element 4.

Figure 3:
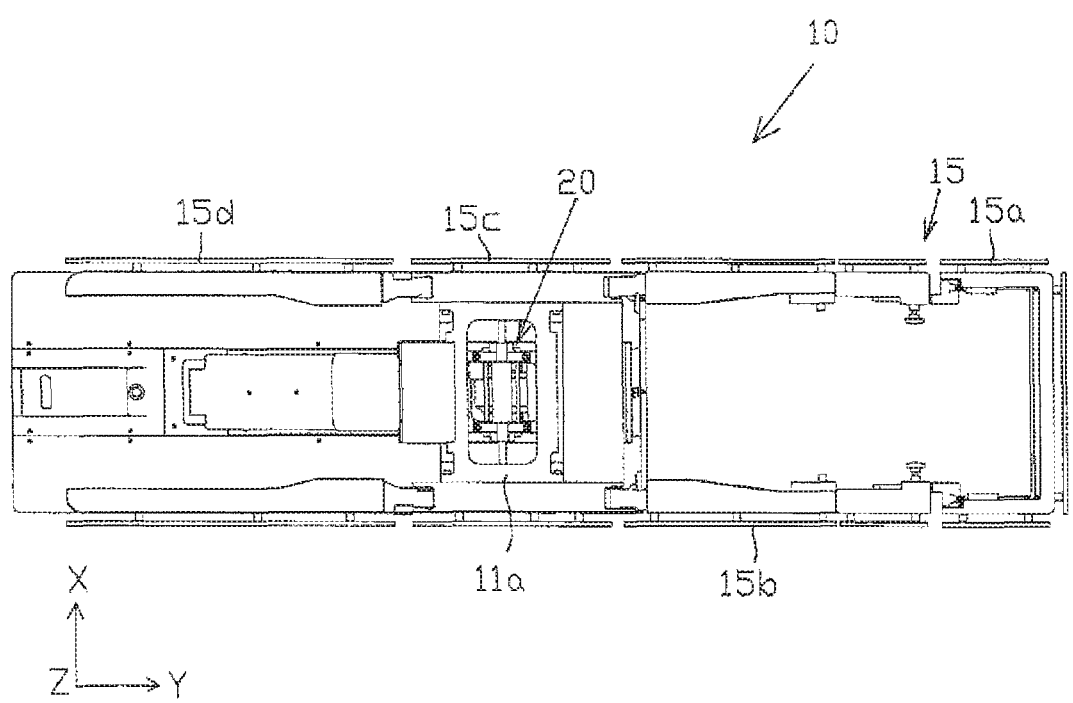
FIG. 3 is a plan view of the surgical operation table from which a top plate of the table is removed.

As illustrated in FIG. 1 to FIG. 3, the table unit 10 includes a table base section 11, and a table 15 that is placed on the table base section 11.

The table 15 is a bed which is for a patient to be laid thereon, includes frame bodies 15a to 15d that are divided into a head part, a back part, a hip part and a leg part respectively, for example, as illustrated in FIG. 1 to FIG. 3, and has a mattress 16 formed of mats and cushions having predetermined thicknesses attached to the frame bodies 15a to 15d, as illustrated in FIG. 1, and has such a size that a patient can lie thereon. The respective frame bodies 15a to 15d are connected by being pin-coupled to be bendable, the respective frame bodies are configured to be turnable in the Z-direction, and are fixable in a predetermined positional relationship by a lock device not illustrated. Note that in the surgical operation table of the present embodiment, the head part moves in the Z-direction by being interlocked with the back part.

In this way, the table 15 of the present embodiment is configured to be of a divided type capable of changing a posture of the patient by turning (bending) the respective frame bodies 15a to 15d as illustrated in FIG. 1(b), and these frame bodies 15a to 15d are configured to be attachable and detachable, and can be replaced with a single plate-shaped member in accordance with contents of a surgical operation and treatment.

Further, for example, at a time of performing a surgical operation of a head of a patient by using an endoscope, a microscope and the like, the surgical operation table S of the present embodiment is used by having the frame body 15a of the head part of the table 15 replaced with an exclusive head fixing instrument not illustrated. The head fixing instrument is an instrument that fixes the head part of the patient, is an instrument including a ring that has a gimbal mechanism and surrounds a head part, and a plurality of pins that are radially screwed onto the ring, and fixes the head part to a set position by butting the plurality of pins to the head part of the patient.

Figure 4:
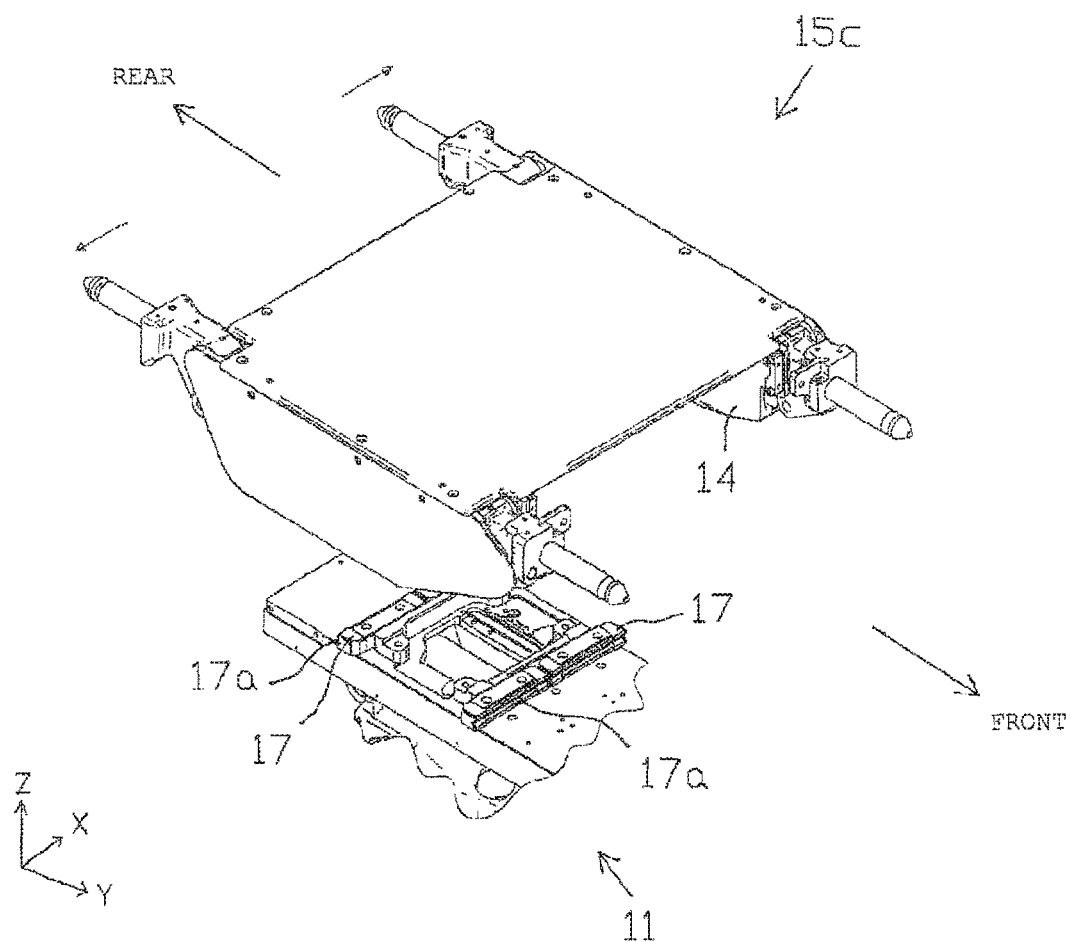
FIG. 4 is a schematic view illustrating a configuration of a slide mechanism of the table.

As illustrated in FIG. 2 and FIG. 4, the table base section 11 supports the table 15 from below, and is disposed under the frame body (hereinafter, referred to as "the hip part frame body 15c") that is disposed at the hip part of the table 15.

At a front and a rear of the table base section 11, slide guide rails 17 and 17 are attached as illustrated in FIG. 4, and grooves 17a that extend along the X-direction (a width direction of the table 15) are formed on side surfaces of the respective slide guide rails 17.

As illustrated in FIG. 3, the hip part frame body 15c includes a support body 11a that supports a hydraulic type cylinder device 20 that functions as a second cylinder device, and the support body 11a is provided with substantially L-shaped projections (not illustrated) that engage with the grooves 17a of the respective slide guide rails 17 illustrated in FIG. 4. The projections engage with the grooves 17a of the respective slide guide rails 17, whereby as illustrated in FIG. 5(b), the hip part frame body 15c is slidable in the X-direction on the table base section 11 as illustrated by the arrows in the drawing.

Note that the respective frame bodies 15a to 15d composing the table 15 are connected to one another, and with movement of the hip part frame body 15c, the other frame bodies 15a, 15b and 15d also move. Accordingly, the table 15 is slidable in a horizontal direction on the table base section 11.

The second cylinder device 20 is configured as a double-acting type cylinder including a cylinder main body 21, and rods 22 that protrude from both side ends of the cylinder main body 21, so that in accordance with an extending motion of one of the rods 22 by a hydraulic pressure, the other rod performs a contracting motion, and an end portion of the one of the rods presses a side surface portion 14 of the hip part frame body 15c.

Figure 5A:
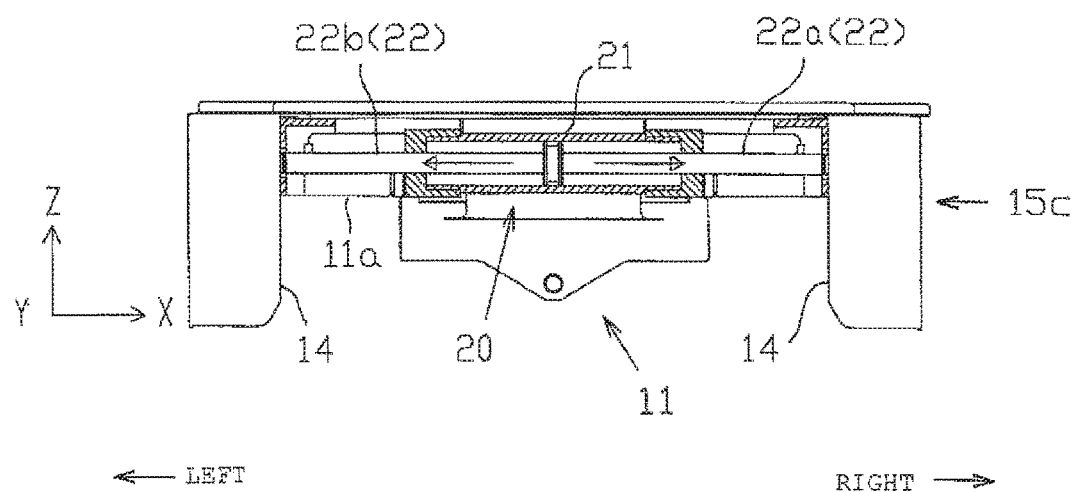
FIG. 5 is a schematic view for explaining a slide motion of the table.
Figure 5B:
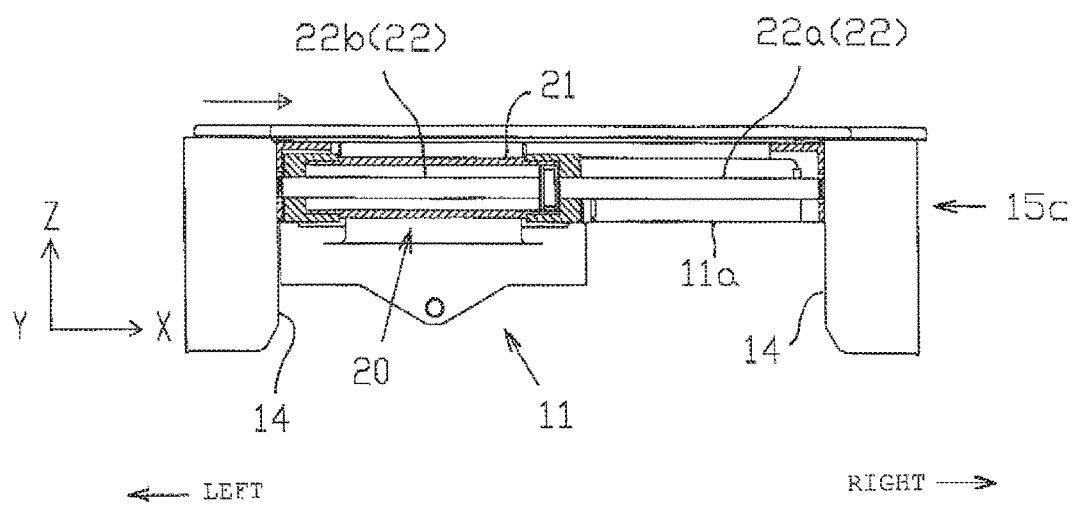

That is, when the second cylinder device 20 is driven, and a rod 22a at a right side is caused to perform an extending motion, for example, the rod 22a at the right side presses the right side surface portion 14 of the hip part frame body 15c, and the table 15 slides in the right direction on the table base section 11, as illustrated in FIG. 5(b). When a rod 22b at a left side is caused to perform an extending motion contrary to the above, the rod 22b at the left side presses a left side surface portion 14 of the hip part frame body 15c, and the table 15 slides in a left direction on the table base section 11. In this way, the table 15 is slidable in the X-direction on the table base section 11 by drive of the second cylinder device 20.

Figure 6A:
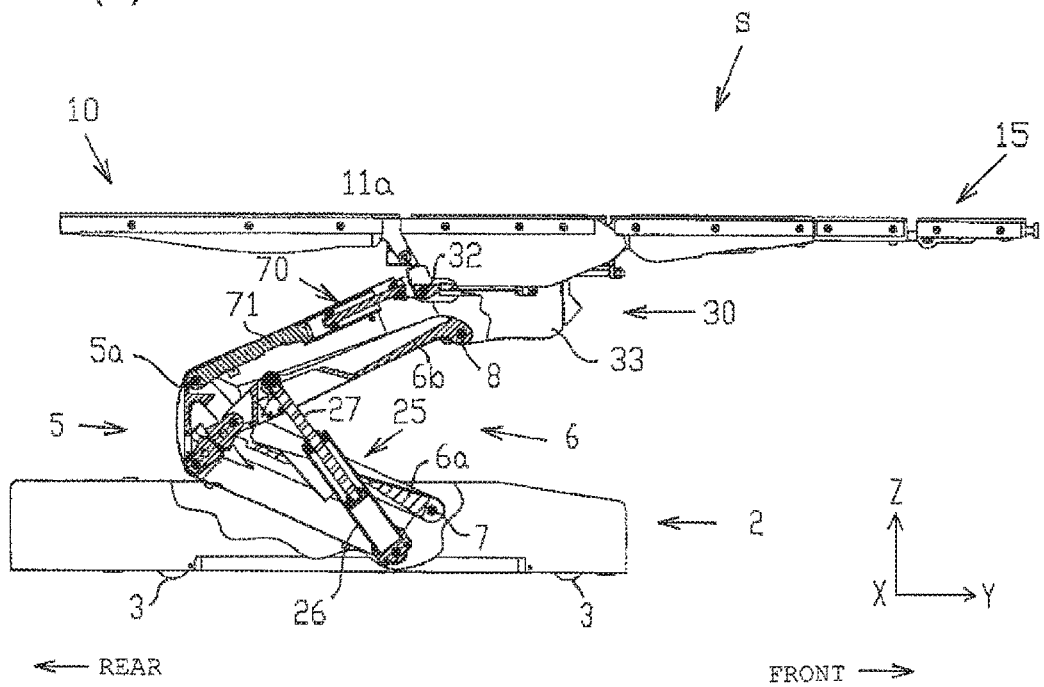
FIG. 6 is a schematic view illustrating a configuration of a link mechanism, FIG. 6(*a*) is a side view of the link mechanism at a time of the table being adjusted to be high, and FIG. 6(*b*) is a side view of a link mechanism at a time of the table being adjusted to be the lowest.

As illustrated in FIG. 2 and FIG. 6, the column 5 has a casing 5a, and includes, in the casing 5a, a link mechanism section 6 in which a plurality of arms 6a and 6b are combined on the base 2, and a hydraulic type cylinder device 25 that connects the respective arms 6a and 6b and functions as a third cylinder device for extending and contracting the link mechanism section 6 in a lengthwise direction.

As illustrated in FIG. 6, the link mechanism section 6 includes the lower arm 6a that is attached to at least the base 2 side via a pivot 7 to be rotatable around an X-axis, and the upper arm 6b that is attached to the table base section 11 side via a lengthwise turning shaft 8 to be rotatable around the X-axis. Further, the third cylinder device 25 is configured by including a cylinder main body 26, and a rod 27 that protrudes from one side end of the cylinder main body 26.

The link mechanism section 6 performs motions by an extending and contracting motions of the rod 27, and the column 5 extends and contracts in the lengthwise direction on the base 2, and is capable of elevating the table 15 to a predetermined height.

Figure 6B:
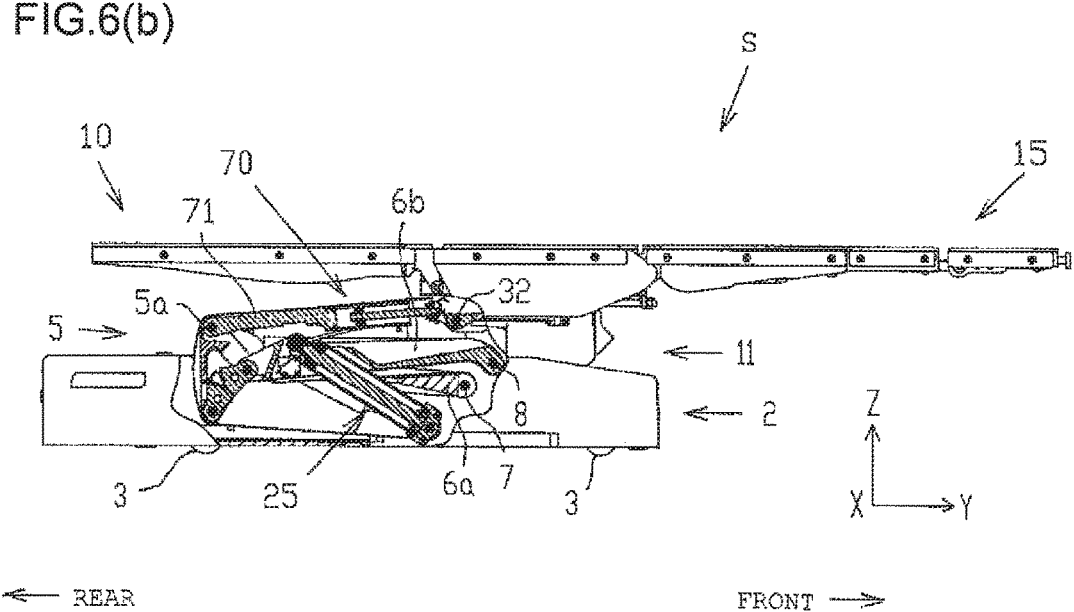

Further, in order to lower a bed of the table, in the link mechanism section 6 of the present embodiment, in a folded state, a connection section at which the table base section 11 and the upper arm 6b are connected via the lengthwise turning shaft 8 is formed to exceed a proximal end side of the lower arm 6a to be curved downward, as illustrated in FIG. 6(b).

The upper and lower arms that compose the link mechanism section 6 are usually formed to have substantially the same lengths, and therefore, the connection section where the table base section 11 and the upper arm 6b are connected is located above the lower arm 6a, but in the surgical operation table S of the present embodiment, the connection section is disposed at a lower side that is forward of the above position, whereby lowering of the bed is achieved.

Figure 7:
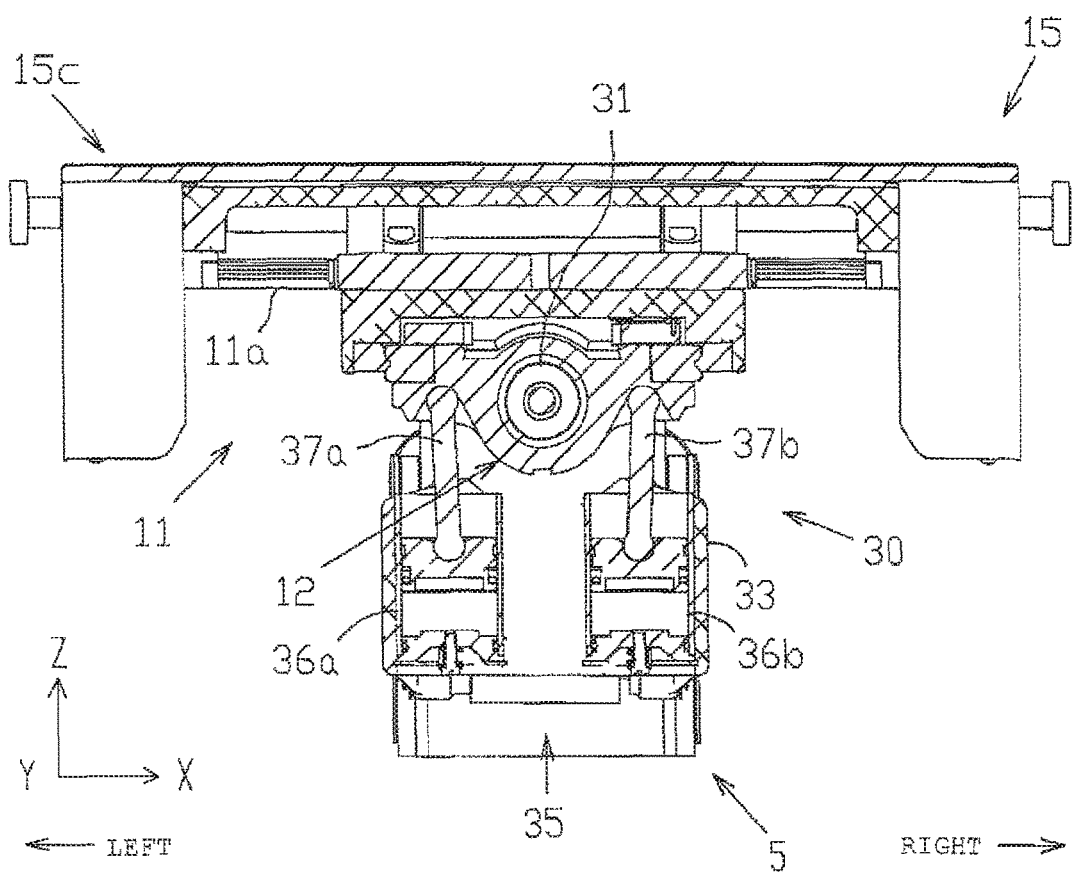
FIG. 7 is a schematic view for explaining a motion of crosswise turning.

Further, as illustrated in FIG. 2 and FIG. 7, the column 5 is attached to the table base section 11 via an inclining mechanism section 30.

The inclining mechanism section 30 has a crosswise turning function of turning (crosswise turning) the table 15 around the Y-axis, and inclining the table 15 in the crosswise direction in FIG. 7, and has a lengthwise turning function of turning (lengthwise turning) the table 15 around the X-axis and inclining the table 15 in the longitudinal direction in FIG. 2. The inclining mechanism section 30 enables the surgical operation table S of the present embodiment to adjust an inclination of the table 15 to a position where the posture of the patient is changed and a doctor can easily perform treatment.

As illustrated in FIG. 6 and FIG. 7, the inclining mechanism section 30 has a crosswise turning shaft 31 that is disposed between the column 5 and the table base section 11 and has an axial line in the Y-direction, and the lengthwise turning shaft 8 that is connected to the upper arm 6b and has an axial line in the X-direction, and the lengthwise turning shaft 8 is housed in a housing 33.

The crosswise turning shaft 31 is turnably connected to a ring-shaped bracket 12 that is provided to protrude downward of a casing 11a of the table base section 11, above the housing 33.

The table 15 is crosswise turnable with the crosswise turning shaft 31 as a support point, and is lengthwise turnable with the lengthwise turning shaft 8 as a support point.

Further, as illustrated in FIG. 7, in the housing 33, a hydraulic type cylinder device 35 that functions as a first cylinder device is provided. The first cylinder device 35 includes a pair of left and right cylinder main bodies 36a and 36b, and rods 37a and 37b that protrude upward from one side ends of the cylinder main bodies 36a and 36b, and the rods 37a and 37b penetrate through the housing 33 and are connected to the bracket 12.

By an extending and contracting motions of the respective rods 37a and 37b by drive of the cylinder device 35, a left side or a right side of the table base section 11 is pushed up or pulled down, whereby a left and right of the table 15 are made inclinable at a predetermined inclination angle with the crosswise turning shaft 31 as the support point.

Further, as illustrated in FIG. 6, the upper arm 6b of the link mechanism section 6 of the column 5 includes two links that are disposed parallel with each other, and one link 71 that is disposed at an upper side is connected to a pivot 32 that is disposed above the lengthwise turning shaft 8 via a hydraulic type cylinder device 70 that functions as a fourth cylinder device. The fourth cylinder device 70 includes a cylinder main body, and a rod protruding upward from a one side end of the cylinder main body, and lengthwise turns the table 15 including the housing 33 with the lengthwise turning shaft 8 as the support point by an extending and contracting motions of the rod, and the table 15 is made inclinable at a predetermined inclination.

Figure 8:
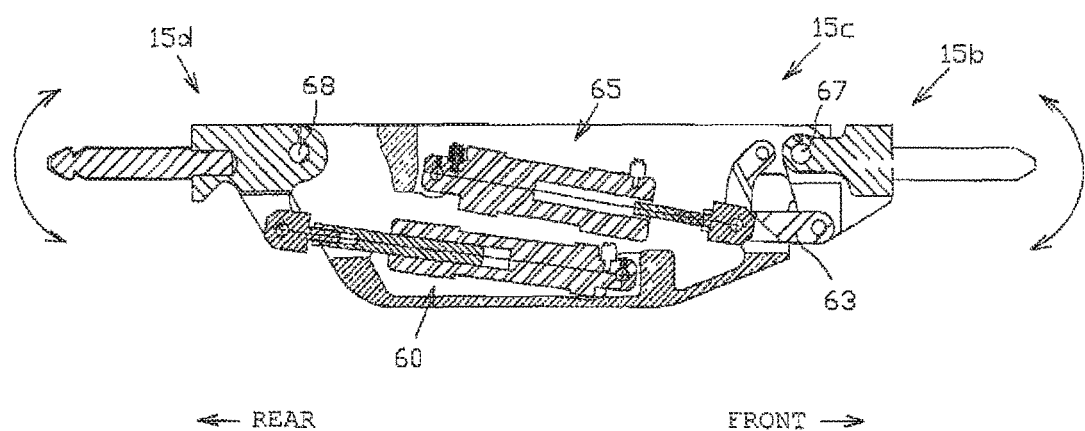
FIG. 8 is a schematic view for explaining a motion of a bending mechanism of the table.

Further, as illustrated in FIG. 8, two hydraulic type cylinder devices 60 and 65 that function as a fifth cylinder device are attached to both left and right sides of the hip part frame body 15c. One of the two cylinder devices 60 and 65 is rotatably attached to the back part frame body 15b via a predetermined connection tool 63, and the other one is rotatably attached to the leg part frame body 15d. By extending and contracting motions of rods of the cylinder devices 60 and 65, the back part frame body 15b or the leg part frame body 15d is made rotatable (bendable) in the Z-axis direction with respect to the hip part frame body 15c, with connection shafts 67 and 68 that connect the respective frame bodies 15c and 15d as support points.

Figure 9:
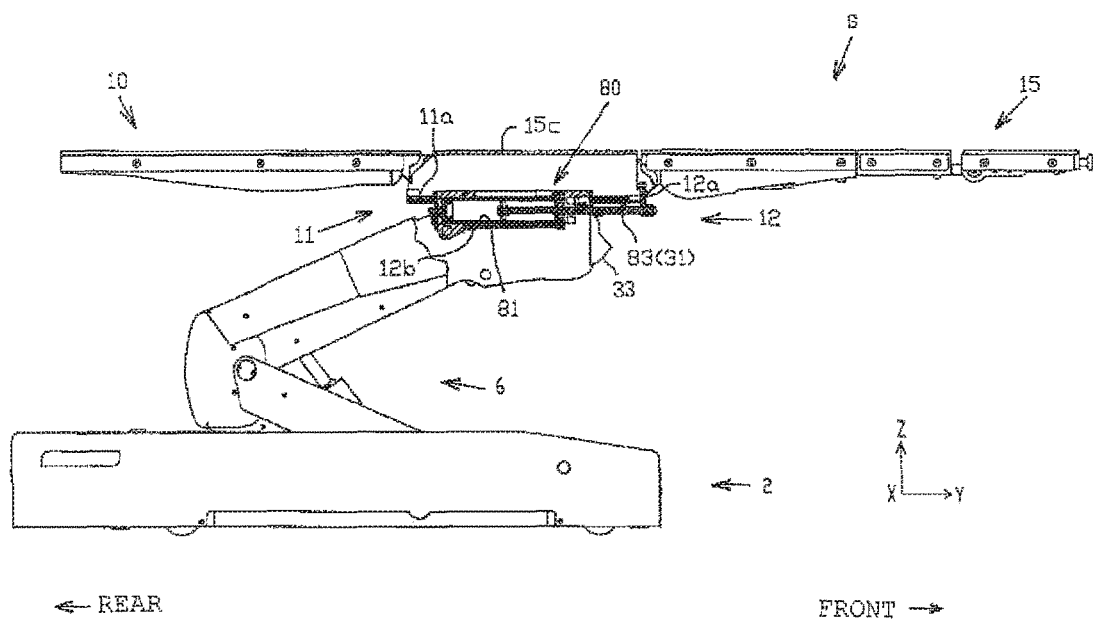
FIG. 9 is a schematic view illustrating a configuration of another slide mechanism of the table.

Further, as illustrated in FIG. 9, the bracket 12 is formed by being divided into an upper frame body 12a and a lower frame body 12b that have sections formed into substantially L-shapes, and the upper frame body 12a is slidable in the longitudinal direction with respect to the lower frame body 12b. The upper frame body 12a is attached to the casing 11a of the table base section 11, the lower frame body 12b is attached integrally with the housing 33, and the table 15 can be slid in the longitudinal direction by movement of the upper frame body 12a.

A hydraulic type cylinder device 80 that functions as a sixth cylinder device is attached to the lower frame body 12b. The sixth cylinder device 80 is configured as a double-acting type cylinder including a cylinder main body 81, and a rod 83 that protrudes from one end of the cylinder main body 81, the cylinder main body 81 is attached to the lower frame body 12b so that the rod 83 is extendable and contractible in the Y-direction, and a tip end of the rod 83 is attached to the upper frame body 12a.

Figure 10A:
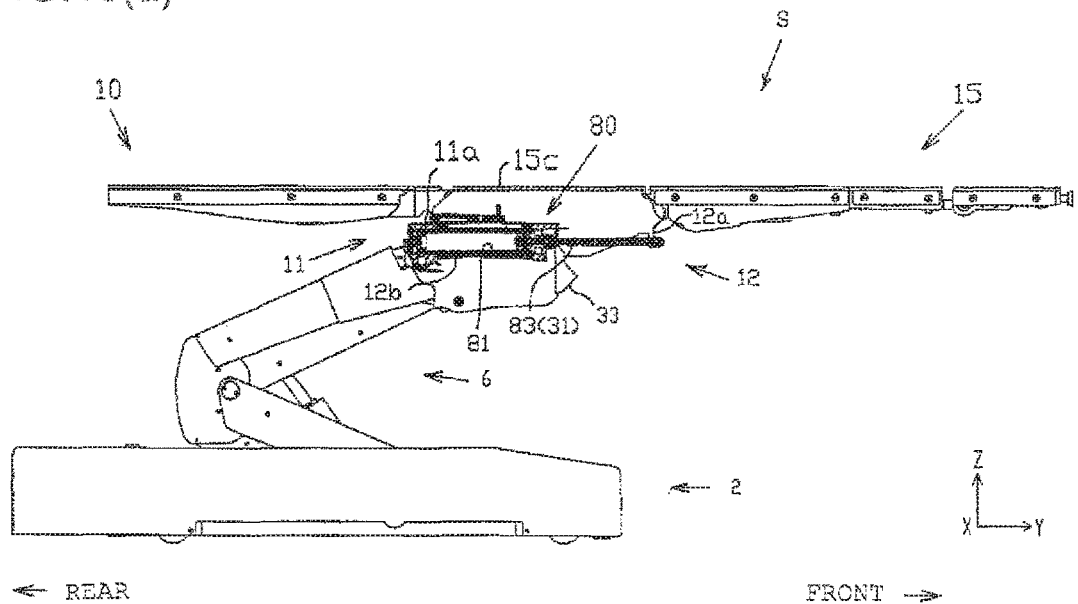
FIG. 10(a) is a schematic view illustrating a state in which the table is moved forward.
Figure 10B:
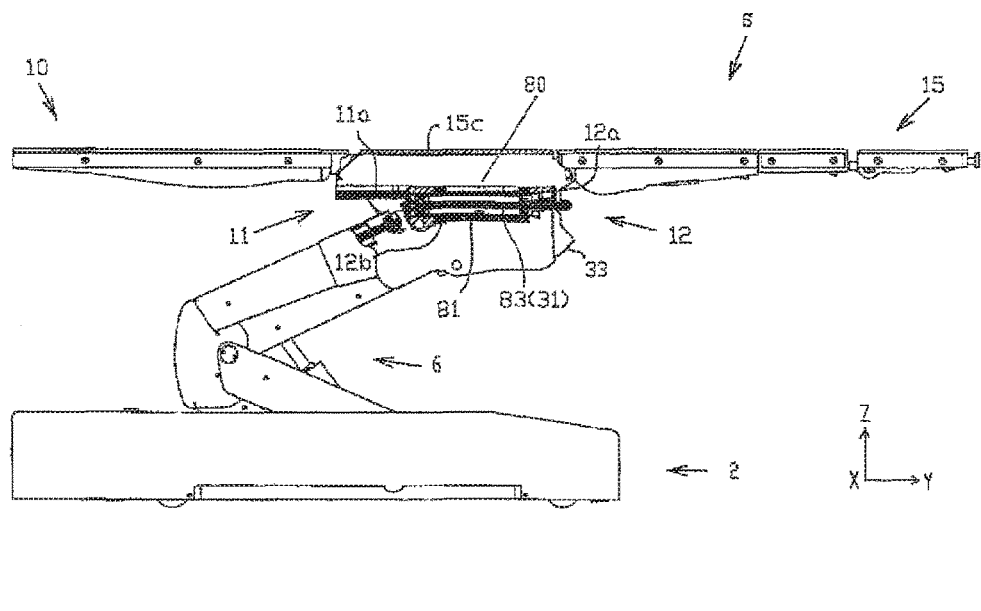
FIG. 10(b) is a schematic view illustrating a state in which the table is moved rearward.

That is, when the sixth cylinder device 80 is driven, and the rod 83 is caused to perform an extending motion, for example, the rod 83 presses the upper frame body 12a and the table 15 slides forward as illustrated in FIG. 10(a). When the rod 83 is caused to perform a contracting motion contrary to the above, the rod 83 pulls back the upper frame body 12a, and the table 15 slides rearward, as illustrated in FIG. 10(b). In this way, the table 15 is slidable in the Y-direction by drive of the sixth cylinder device 80.

Further, in the surgical operation table S of the present embodiment, the rod 83 of the sixth cylinder device 80 functions as the crosswise turning shaft 31 which becomes the support point at the time of crosswise turning the table 15.

Next, a basic motion example of the surgical operation table will be described.

In the surgical operation table, predetermined motions are performed by drive of the respective first to sixth cylinder devices 35, 20, 25, 70, 60, 65 and 80. More specifically, by the first cylinder device 35, a horizontal moving motion in the X-direction of the table 15 is performed, and by the sixth cylinder device 80, a horizontal moving motion in the Y-direction of the table 15 is performed. Further, the crosswise turning motion of the table 15 is performed by the second cylinder device 20, the elevating motion of the table 15 is performed by the third cylinder device 25, the lengthwise turning motion of the table 15 is performed by the fourth cylinder device 70, and bending motions of the respective sections of the table 15 is performed by the fifth cylinder devices 60 and 65.

Note that although the motions of the hydraulic type cylinder devices are a known technique, and therefore, detailed explanation of the motions will be omitted, double-acting type cylinders, for example, are used as the respective first to sixth cylinder devices 35, 20, 25, 70, 60, 65 and 80, ports where the working oil that is a liquid enters and exits are formed at both ends of the cylinder main body, and the respective ports are respectively connected to a predetermined hydraulic pressure generating device via valve devices by predetermined tubes. Subsequently, the hydraulic pressure generating device is driven and the valve devices are operated, whereby the working oil enters and exits each of the ports of the respective first to sixth cylinder devices 35, 20, 25, 70, 60, 65 and 80, and thereby extends and contracts rods, to cause the link mechanism section 6 of the table 15 or the column 5 to perform motions.

Next, another motion example of the surgical operation table S will be described with use of FIG. 11 to FIG. 14. The surgical operation table S of the present embodiment is capable of causing a plurality of cylinder devices to perform motions cooperatively, in addition to normal motions that cause the respective cylinder devices 35, 20, 25, 70, 60, 65 and 80 to perform motions individually as described above.

Note that it is possible to perform switch of the motions by using the remote controller and the display element 4.

The respective cylinder devices 35, 20, 25, 70, 60, 65 and 80 perform predetermined motions as described above by individual drive, and the surgical operation table S of the present embodiment has an isocenter function, and drives the first and second cylinder devices 35 and 20 cooperatively, or drives the third, fourth, and sixth cylinder devices 25, 70 and 80 cooperatively. Note that the isocenter function refers to a function of crosswise turning or lengthwise turning the table 15 almost without moving the position (a center axis) of the head part of the patient.

Figure 12:
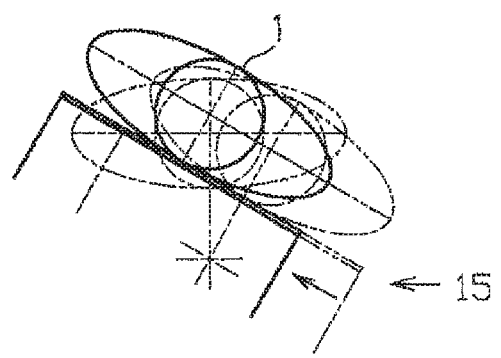
FIG. 12 is a schematic diagram for explaining an isocenter function at the time of the crosswise turning motion.

First, the isocenter function at a time of crosswise turning will be described. When the table 15 is crosswise turned to the right side, for example, in a state where a patient 1 is laid on the table 15, as illustrated in FIG. 12, the position of the patient 1 deviates as illustrated by the two-dot chain line as compared with a case where the table 15 is in a horizontal state. Therefore, in the present embodiment, a motion of sliding the table 15 to the left side (an opposite direction) by using the second cylinder device 20 as illustrated by the arrow in FIG. 12, is performed with the motion of crosswise turning the table 15 to the right side by using the first cylinder device 35, whereby a positional deviation of the patient accompanying the crosswise turning motion is inhibited.

A specific motion example of the surgical operation table and hydraulic system will be described by using FIG. 11. Note that valve devices 43 and 44 that will be described below are controlled by the control device of the surgical operation table.

The first cylinder device 35 adjusts a crosswise turning angle of the table 15 by inclining the table 15 crosswise, and the second cylinder device 20 horizontally slides the table 15 crosswise on the table base section 11. As described above, the surgical operation table S of the present embodiment prevents the position of the head part of the patient from moving (causes a positional deviation) by sliding the table 15, as well as inclining the table 15 crosswise.

Figure 11:
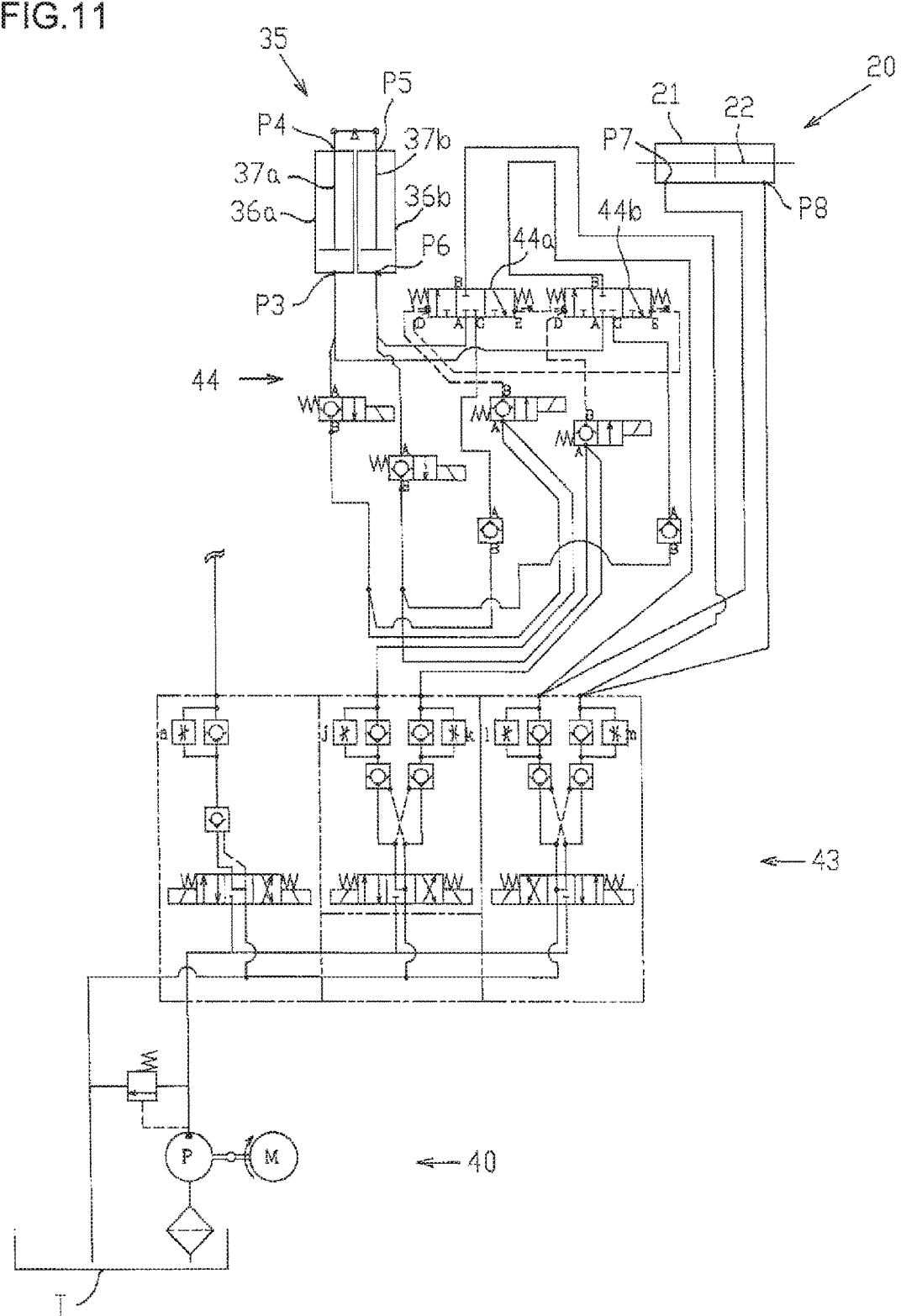
FIG. 11 is a schematic diagram illustrating a configuration example of a hydraulic system of the surgical operation table at a time of a crosswise turning motion.

As illustrated in FIG. 11, ports P3 to P6 are respectively formed at both end portions of the cylinder main bodies 36 at the left and right of the first cylinder device 35, and ports P7 and P8 are formed at both end portions of the cylinder main body 21 of the second cylinder device 20.

Ports P4 and P5 at one sides that are formed in the left and right cylinder main bodies 36a and 36b of the first cylinder device 35 are directly connected to each other by a predetermined tube, and the respective other ports P3 and P6 of the left and right cylinder main bodies 36a and 36b are connected to a hydraulic pressure generating device 40, and the ports P7 and P8 which are formed at both end portions of the cylinder main body 21 of the second cylinder device 20, via the valve devices 43 and 44. Further, the ports P7 and P8 which are formed in the cylinder main body 21 of the second cylinder device 20 are connected to the hydraulic pressure generating device 40 via the valve device 43.

When the hydraulic pressure generating device 40 is driven and the valve devices 43 and 44 are operated, the port P3 of the cylinder main body 36a at the left side of the first cylinder device 35 is caused to communicate with a pump P, for example, the port P6 of the cylinder main body 36b at the right side is caused to communicate with the port P8 at the right end portion of the first cylinder device 20, and the port P7 at the left end portion of the second cylinder device 20 is caused to communicate with an oil tank T, the rod 37a of the cylinder main body 36a at the left side of the first cylinder device 35 performs an extending motion, the rod 37b of the cylinder main body 36b at the right side performs a contracting motion, the rod 22 of the second cylinder device 20 performs an extending motion to the left side, and the table 15 slides to the left side while inclining to the right side.

When the port P6 of the cylinder main body 36b at the right side of the first cylinder device 35 is caused to communicate with the pump P, the port P3 of the cylinder main body 36a at the left side is caused to communicate with the port P7 at the left end portion of the second cylinder device 20, and the port P8 at the right end portion of the second cylinder device 20 is caused to communicate with the oil tank T, the rod 37b of the cylinder main body 36b at the right side of the first cylinder device 35 performs an extending motion, the rod 37a of the cylinder main body 36a at the left side performs a contracting motion, the rod 22 of the second cylinder device 20 performs an extending motion to the right side, and the table 15 slides to the right side while inclining to the left side.

In this way, the surgical operation table S of the present embodiment causes the working oil (return oil) that returns from the respective ports P3 and P6 to the oil tank T at the time of driving the first cylinder device 35 to flow into the ports P7 and P8 at one side of the second cylinder device 20, and thereby causes the crosswise turning motion of the table 15 and the slide motion in the X-direction of the table 15 to be performed, and is capable of simultaneously performing the inclining motion of the table 15 and the slide motion of the table 15 smoothly.

Note that in the present embodiment, the working oil that returns to the oil tank T from the first cylinder device 35 is supplied to the second cylinder device 20, and prevents insufficiency of supply of the working oil with a simple structure by making a cylinder diameter (a sectional area) of the cylinder main body 21 of the second cylinder device 20 smaller than cylinder diameters of the cylinder main bodies 36a and 36b of the first cylinder device 35, by considering that the supply amount of the working oil becomes insufficient.

Next, an isocenter function at a time of lengthwise turning will be described. When the table 15 is lengthwise turned in such a manner as to lower a rear side, for example, from a state where the patient 1 is horizontally laid on the table 15, as illustrated in FIG. 14, the position of the head part of the patient 1 is deviated rearward and upward as compared with the case where the table 15 is in the horizontal state. Therefore, in the present embodiment, a positional deviation of the patient accompanying the lengthwise turning motion is inhibited by performing a motion of sliding the table 15 forward by using the sixth cylinder device 80 as illustrated by an arrow A in FIG. 14 as well as a motion of lengthwise turning the table 15 so that the rear side of the table 15 lowers by using the fourth cylinder device 70, and further performing a motion of lowering the table 15 by using the third cylinder device 25 as illustrated by an arrow B in FIG. 14.

Figure 13:
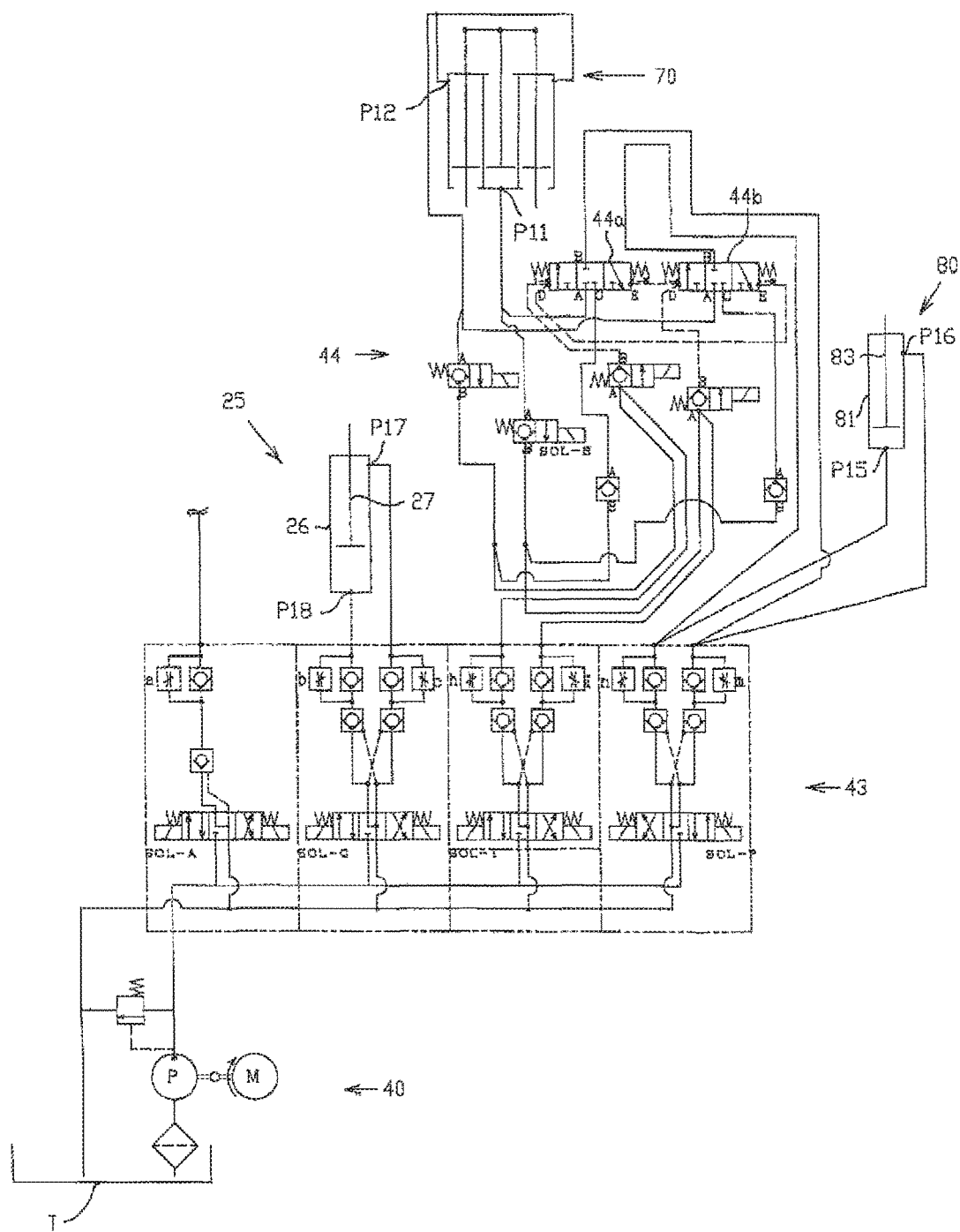
FIG. 13 is a schematic diagram illustrating a configuration example of the hydraulic system of the surgical operation table at a time of a lengthwise turning motion.

A specific motion example of the surgical operation table and hydraulic system will be described with use of FIG. 13. Note that the valve devices 43 and 44 that will be described below are controlled by the control device of the surgical operation table.

The third cylinder device 25 adjusts a height of the table 15 by elevating the table lengthwise, the fourth cylinder device 70 adjusts the lengthwise turning angle of the table 15 by inclining the table 15 longitudinally, and the sixth cylinder device 80 horizontally slides the table 15 in the longitudinal direction. As described above, the surgical operation table S of the present embodiment prevents the position of the head part of the patient from moving (causing a positional deviation) by lengthwise turning the table 15 in the horizontal state to incline the table 15 longitudinally, sliding the table 15 rearward, and further elevating the table 15 to adjust the height.

Ports P11 and P12 are formed at both end portions of the cylinder main body of the fourth cylinder device 70, ports P15 and P16 are formed at both end portions of the cylinder main body of the sixth cylinder device 80, and ports P17 and P18 are formed at both end portions of the cylinder main body of the third cylinder device 25.

The respective ports P11 and P12 which are formed in the cylinder main body of the fourth cylinder device 70 are connected to the hydraulic pressure generating device 40, and the ports P15 and P16 which are formed at both the end portions of the cylinder main body 81 of the sixth cylinder device 80, via the valve devices 43 and 44. Further, the ports P15 and P16 which are formed in the cylinder main body 81 of the sixth cylinder device 80, and the ports P17 and P18 which are formed in the cylinder main body of the third cylinder device 25 are respectively connected to the hydraulic pressure generating device 40 via the valve device 43.

When the hydraulic pressure generating device 40 is driven, the valve devices 43 and 44 are operated, and the table in the horizontal state is lengthwise turned as illustrated in FIG. 14, for example, the port P12 of the cylinder main body of the fourth cylinder device 70 is caused to communicated with the pump P, the port P11 is caused to communicate with the port P15 of the sixth cylinder device 80, and the port P16 of the sixth cylinder device 80 is caused to communicate with the oil tank T. In this manner, the rod of the cylinder main body of the fourth cylinder device 70 performs a contracting motion, the rod 83 of the sixth cylinder device 80 performs an extending motion forward, and the table 15 slides in the forward direction while the rear side of the table 15 lengthwise turns downward.

When the table 15 is returned to the horizontal state from the state where the table 15 is lengthwise turned as illustrated in FIG. 14, the port P11 of the cylinder main body of the fourth cylinder device 70 is caused to communicate with the pump P, the port P12 is caused to communicate with the port P16 of the sixth cylinder device 80, and the port P15 of the sixth cylinder device 80 is caused to communicate with the oil tank T. In this manner, the rod of the cylinder main body of the fourth cylinder device 70 performs an extending motion, the rod 83 of the sixth cylinder device 80 performs a contracting motion rearward, and the table 15 slides in the rearward direction while the rear side of the table 15 is lengthwise turned upward.

In this way, the surgical operation table S of the present embodiment causes the lengthwise turning motion of the table 15 and the slide motion in the Y-direction of the table 15 to be performed by causing the working oil (the return oil) that returns to the oil tank T from the respective ports P11 and P12 at a time of driving the fourth cylinder device 70 to flow into the ports P15 and P16 at one side of the sixth cylinder device 80, and is capable of simultaneously performing the inclining motion of the table 15 and the slide motion of the table 15 smoothly.

Further, in the present embodiment, adjustment in the height direction of the table 15 is needed when the lengthwise turning motion is performed. An extension and contraction amounts of the rod 27 of the third cylinder device 25 which adjusts the height direction of the table 15 are subjected to extension and contraction control, in accordance with an extension and contraction amounts of the rod of the fourth cylinder device 70. More specifically, when a contracting motion of the rod of the fourth cylinder device 70 is performed (refer to FIG. 14) in the horizontal state of the table 15, the table 15 is lowered by driving the fourth cylinder device 70 and causing the rod 27 of the third cylinder device 25 to perform a contracting motion. When the table 15 is returned to the horizontal state from the state where the table 15 is lengthwise turned as illustrated in FIG. 14, the rod of the fourth cylinder device 70 is caused to perform an extending motion and the rod 27 of the third cylinder device 25 is caused to perform an extending motion to raise the table 15.

Likewise, when the rod of the fourth cylinder device 70 is caused to perform an extending motion in the horizontal state of the table 15, the rod 83 of the sixth cylinder device 80 is caused to perform an extending motion with drive of the fourth cylinder device 70 to slide the table 15 forward, and the rod 27 of the third cylinder device 25 is further caused to perform a contracting motion to lower the table 15.

When the table 15 is returned to the horizontal state, the rod 83 of the sixth cylinder device 80 is caused to perform a contracting motion with the contracting motion of the fourth cylinder device 70 to slide the table 15 rearward, and the rod 27 of the third cylinder device 25 is caused to perform an extending motion to raise the table 15.

Note that the hydraulic system may be constructed so as to also supply the working oil which returns to the oil tank T from the respective ports P11 and P12 at the time of driving the fourth cylinder device 70 to the third cylinder device 25 as well as the sixth cylinder device 80. Thereby, the slide motion in the Y-direction of the table 15, and the elevating motion of the table 15 can be performed with the lengthwise turning motion of the table 15, and the inclining motion of the table 15, the slide motion of the table 15 and the elevating motion of the table 15 can be simultaneously performed smoothly.

As described above, the surgical operation table S of the present embodiment is the surgical operation table S including the table 15 for laying a patient thereon, the first to the sixth cylinder devices 35, 20, 25, 70, 60, 65 and 80 that function as the motion mechanism sections that slide, crosswise turn, lengthwise turn and elevate the table 15, and the base 2 which supports the table 15 via the motion mechanism sections, and includes the hydraulic system that functions as position holding device that crosswise turns or lengthwise turns the table 15 without moving the position of the head part of the patient laid on the table 15.

The hydraulic system slides the table 15 in an opposite direction from a crosswise turning direction of the table 15 at the time of the crosswise turning motion of the table 15 when crosswise turning.

Further, when the hydraulic system lengthwise turns the table 15 from the horizontal state, the hydraulic system slides the table 15 in the forward direction and elevates the table 15 at the time of the lengthwise turning motion of the table 15, and when the hydraulic system returns the table 15 to the horizontal state from the lengthwise turned state, the hydraulic system slides the table 15 in the rearward direction and elevates the table 15 at the time of the lengthwise turning motion of the table 15.

According to the surgical operation table S of the present embodiment which performs motions like this, it is possible to move the table 15 with a point in a space above the table 15 as the center, and the posture of the patient can be changed by crosswise turning the table 15 almost without moving the position of the head part of the patient.

Further, even when the table 15 inclines, the position of the head part of the patient laid on the table 15 hardly moves, and therefore, especially in the surgical operation using an endoscope and a microscope, the state of the head part can be observed without requiring adjustment or the like by changing the posture of the patient.

Note that the present embodiment is only one mode, and the present invention is not limited to this mode. For example, for the mechanism of the inclining mechanism section 30 of the present embodiment, a generally well-known mechanism can be properly used. Further, the amount of the working oil which is supplied to the first cylinder device 35 can be at least a part of the working oil which is discharged to the tank T side from the third cylinder device 25, and is adjusted by the valve devices being properly controlled in accordance with the size of the patient, the diameters of the tubes that connect the ports and the like.

Further, in the respective cylinder devices which are used in the present embodiment, double-acting type cylinders are used, but single-acting type cylinders may be applied.

REFERENCE SIGNS LIST

S Surgical operation table
2 Base
5 Column
11 Table base section
15 Table
30 Inclining mechanism section

The invention claimed is:

1. A surgical operation table comprising:
   a table comprising a length, a bottom surface, and a top surface that is opposite the bottom surface, the table configured to support a patient laid thereon;
   a plurality of cylinder devices that move the table by supplying or discharging a working oil and by extending or contracting a rod by a pressure of the working oil;
   wherein the plurality of cylinder devices comprise:
      a crosswise-turning cylinder device that crosswise turns the table to a first predetermined inclination angle relative to a left-right direction of the patient laid on the table; and
      a lateral-slide cylinder device that laterally slides the table in the left-right direction of the patient;
   wherein the plurality of cylinder devices move the table to perform an isocenter function for a predetermined position of the patient laid on the table by cooperatively driving the crosswise-turning cylinder device and the lateral-slide cylinder device by using the working oil.

2. The surgical operation table according to claim 1, wherein the plurality of cylinder devices move to perform the isocenter function for the predetermined position of the patient laid on the table by driving the lateral-slide cylinder device to slide the table to a left side while the crosswise-turning cylinder device crosswise turns the table to incline to a right side, or driving the lateral-slide cylinder device to slide the table to the right side while the crosswise-turning cylinder device crosswise turns the table to include to the left side.

3. The surgical operation table according to claim 1, wherein when one of the crosswise-turning cylinder device and the lateral-slide cylinder device is driven, a return oil which is the working oil returning to an oil tank is caused to flow into the other cylinder device of the crosswise-turning cylinder device and the lateral-slide cylinder device to cooperatively drive the crosswise-turning cylinder device and the lateral-slide cylinder device using the working oil.

4. The surgical operation table according to claim 1, wherein a cylinder diameter of one of the crosswise-turning cylinder device and the lateral-slide cylinder device which supplies the working oil is greater than a cylinder diameter of the other cylinder device of the crosswise-turning cylinder device and the lateral-slide cylinder device.

5. The surgical operation table according to claim 1, wherein the plurality of cylinder devices further comprise:
a lengthwise-turning cylinder device that lengthwise turns the table to a second predetermined inclination angle relative to a head-foot direction of the patient laid on the table;
a longitudinal-slide cylinder device that longitudinally slides the table in the head-foot direction of the patient; and
an elevating cylinder device that elevates the table in a vertical direction of the patient,
wherein the plurality of cylinder devices move the table to perform the isocenter function for a second predetermined position of the patient laid on the table by cooperatively driving the lengthwise-turning cylinder device, the longitudinal-slide cylinder device, and the elevating cylinder device by using the working oil.

* * * * *